(12) United States Patent  
Fouillet et al.

(10) Patent No.: US 7,052,244 B2  
(45) Date of Patent: May 30, 2006

(54) DEVICE FOR DISPLACEMENT OF SMALL LIQUID VOLUMES ALONG A MICRO-CATENARY LINE BY ELECTROSTATIC FORCES

(75) Inventors: Yves Fouillet, Voreppe (FR); Raymond Charles, St. Jean de Moirans (FR); Olivier Constantin, Grenoble (FR); Hubert Jeanson, St. Martin d'Uriage (FR)

(73) Assignee: Commissariat a l'Energie Atomique, Paris (FR)

( * ) Notice: Subject to any disclaimer, the term of this patent is extended or adjusted under 35 U.S.C. 154(b) by 435 days.

(21) Appl. No.: 10/457,375

(22) Filed: Jun. 10, 2003

(65) Prior Publication Data

US 2004/0007377 A1    Jan. 15, 2004

(30) Foreign Application Priority Data

Jun. 18, 2002    (FR) .................................. 02 07477

(51) Int. Cl.  
*F04F 11/00* (2006.01)
(52) U.S. Cl. ....................................................... 417/48
(58) Field of Classification Search ................... 417/48  
See application file for complete search history.

(56) References Cited

U.S. PATENT DOCUMENTS

| 4,569,575 A | 2/1986 | Le Pesant et al. |
| 5,181,016 A | 1/1993 | Lee |
| 6,790,011 B1 * | 9/2004 | Le Pesant et al. ............ 417/48 |

FOREIGN PATENT DOCUMENTS

| FR | 2 794 039 | 12/2000 |
| WO | WO 00/73655 | 12/2000 |

* cited by examiner

*Primary Examiner*—Michael Koczo, Jr.  
(74) *Attorney, Agent, or Firm*—Oblon, Spival, McClelland, Maier & Neustadt, P.C.

(57) ABSTRACT

The invention relates to a device for displacement of at least a small volume of liquid (5) under the effect of an electrical control, including a substrate (1) provided with first electrically conducting means (2), the device also comprising second electrically conducting means (3) arranged facing the first electrically conducting means (2), the first electrically conducting means and the second electrically conducting means possibly being connected to electrical power supply means to enable the application of electrostatic forces to the small liquid volume (5). The second electrically conducting means include at least one conducting wire (3) arranged parallel to the substrate and at a fixed distance from the substrate to enable displacement of the small volume of liquid (5) along said conducting wire (3) under the effect of the applied electrostatic forces.

22 Claims, 8 Drawing Sheets

DEVICE FOR DISPLACEMENT OF SMALL LIQUID VOLUMES ALONG A MICRO-CATENARY LINE BY ELECTROSTATIC FORCES

BACKGROUND OF THE INVENTION

1. Field of the Invention

The invention relates to a device for manipulation of small volume droplets consisting of a few nanoliters to a few microliters. The displacement device uses electrostatic forces to displace small liquid volumes.

2. Description of the Background Art

Liquids are increasingly important in small components. Thus, labs-on-chips are used in many studies, mainly for biology, chemistry and optics. In some cases, micro-fluidics consists of making small volumes of liquid circulate in micro-machined ducts. For example, this means that a biological protocol can be applied on a very small sample volume. At the present time it is recognized that there are many advantages in minimizing analysis volumes, for example cost reductions, and improved speed and sensitivity.

However, miniaturizing the section of ducts also introduces a large number of difficulties. Firstly, it is difficult to control fluid displacements in these micro-ducts. Secondly, physicochemical interactions between liquids and the walls become predominant. Capillarity phenomena play an essential role, which requires very high quality surface conditions (roughness, physicochemistry). Similarly, phenomena for absorption of biological entities at the wall surface can limit reaction efficiencies. Thus, it is often necessary to apply specific surface treatments on the walls of ducts or to add different substances in biological protocols to limit these absorption phenomena. The article entitled "Miniaturized flow-through PCR with different template types in a silicon chip thermocycler" by Ivonne Schneegaβ et al., Lab on a Chip, 2001, 1, pages 42–49, contains an example.

Another difficulty with micro-fluidics in micro-ducts is connecting the component to the outside world. Connection of capillaries to a micro-component is one difficulty encountered in making labs on chips. Furthermore, inputs/outputs of the various liquids from or to external fluid storage systems have to be managed, while limiting dead volumes.

Another method of displacing small fluid volumes consists of manipulating an interface between two immiscible fluids. For example, document FR-A-2 548 431 divulges a device with electrical control of the displacement of a dielectric liquid. A liquid droplet is placed between two planes containing electrode pairs. The permittivity of the liquid droplet is greater at its environment defined by the space between the two planes comprising the electrodes. The displacement is controlled electrically by applying electric voltages to the electrode pairs. In this document, the displacement is explained by the existence of a dielectric force resulting from a difference in permittivity between the droplet and its environment and by electric field gradients resulting from applied voltages.

More precisely, the dielectric force tends to attract the fluid with a higher permittivity towards areas in which the field is more intense. This force is capable of overcoming surface tension forces, which explains displacement of the droplet.

Document FR-A-2 548 431 also recommends that the wettability of the liquid on the walls should be low. A silane (aminopropyltrimethoxysilyl chloride) type surface treatment is used to make the surfaces only very slightly wetting. Therefore, this principle is applicable to isolating liquids, however a very slightly conducting liquid may also be used provided that an alternating voltage is used. The article "Mouvement d'un fluide en présence d'un champ électrique—Movement of a fluid in the presence of an electric field" by Pierre Atten, D 2850, Techniques de l'Ingénieur, Paris, describes the existence of electrostatic forces within fluids. In particular, it states that for two "perfectly insulating immiscible media and for an alternating voltage with a sufficiently high frequency f (f>>1/τ, where τ is the characteristic relaxation time of the space charge), only the permittivity skip at the interface contributes to the electric force".

A configuration similar to the description in document FR-A-2 548 431 is described in the article "Electrowetting-based actuation of liquid droplets for microfluidic applications" by Michael G. Pollack et al., Applied Physics Letters, Vol. 77, No. 11, pages 1725 and 1726, Sep. 11, 2000. A water droplet is placed between two planes containing electrodes. The electrodes are covered with an electrically insulating layer that is made very hydrophobic by a thin deposit of Teflon®. The displacement principle is explained by electrocapillarity or electrowetting phenomena. The component presented in this article is capable of displacing 0.7 to 1 μl droplets with voltages of 120 V.

There are also methods of displacing conducting liquid droplets. For example, the article "Microactuation by continuous electrowetting phenomenon and silicon deep RIE process", by Junghoon Lee et al., DSC-Vol. 66, Micro-Electro-Mechanical Systems (MEMS)-1998, ASME 1998 presents a method for displacing mercury droplets in a duct full of electrolyte by electrowetting.

Electrocapillarity has been studied for a long time (Lippman, 1875). A formulation is given in the article "Electrocapillarité et mouillage de films isolants par l'eau—Electrocapillarity and wetting of insulating films by water", by Bruno Berge, C. R. Acad. Sci. Paris, t.317, series II, pages 157–153, 1993. A non-dielectric liquid droplet is deposited on a substrate comprising an electrode covered by an insulator. A second electrode is dipped into the droplet. The droplet spreads when an electric voltage is applied between the two electrodes. In this article, the wetting angle of the droplet on the surface θ is expressed as a function of the electrostatic voltage V applied between the two electrodes by the relation (1):

$$\cos\theta(V) = \cos\theta(O) + \frac{1}{2}\frac{\varepsilon_r}{e\gamma}V^2 \qquad (1)$$

where $\varepsilon_r$ is the dielectric coefficient of the insulating layer with thickness e, and γ is the liquid-gas surface tension.

The article "Moving droplets on asymmetrically structured surfaces", by O. Sandre et al., Physical Review E., Vol. 60, No. 3, September 1999, uses theory and experiment to demonstrate that initiating a vibration of a droplet placed between two substrates with an asymmetric structure can cause displacement of this droplet. An asymmetric structure is described like grooving in a saw tooth shape. The droplet is made to vibrate by the application of an electrostatic field oscillating between two electrodes placed on each of the two substrates in turn.

The disadvantage of the devices described above is that the droplets have to be confined between two planes or in a duct. This makes assembly and use of the component complex. Capillary connection problems arise that have already been identified for micro-fluidics in ducts, in which electrical connections also have to be taken into account. There are also risks of phenomena for absorption of biological entities on the two planes confining the droplets.

Another method of displacing droplets was presented in the article "Electrical Actuation of liquid droplets for microreactor applications" by Masao Washizu, IEEE Industry Applications Society, Annual meeting, New Orleans, La., Oct. 5–9, 1997, and more recently in "Droplet Manipulation on a Superhydrophobic Surface for Microchemical Analysis" article by Altti Torkkeli et al., Transducers' 01 Eurosensors XV.

In this case, the system is open. A droplet is deposited directly on a surface. The surface comprises several inter-digitized electrodes covered by an insulating layer. The surface is made very hydrophobic. Activation is based on the presence of electrostatic forces generated by electrodes placed under the droplet. By modifying the potential of electrodes, the distribution of Maxwell stresses on the surface of the droplet is modified, and M. Washizu has demonstrated that this electrostatic pressure can cause displacement of the droplet.

Unlike the previous examples, this method requires a large number of electrodes. Furthermore, an operation to structure the insulating layer is described in the article by M. Washizu to guide the droplet during its displacement.

The latter two articles are insistent about the hydrophobic nature of the surfaces, and particularly Torkelli et al use demineralized water as the liquid. This can be very limiting for some biological applications, in which the addition of reagents makes the liquids wetting.

In prior art described above, application of an electrostatic field obtained with a set of electrodes causes the displacement of a liquid droplet. Different interpretations were given depending on the configurations of electrodes or the electrical properties of liquids (insulating, or weakly or strongly conducting liquids). Thus, there was a question of the strength of the dielectric volume, electro-capillarity, electro-wetting or electrostatic pressure. All of these various phenomena will be referred to as "electrostatic forces" throughout the rest of this description, although this term is not strictly accurate.

SUMMARY OF THE INVENTION

This invention was designed to overcome the disadvantages that arise with devices according to prior art.

Its purpose is a device for displacement of at least a small volume of liquid under the effect of an electrical control including a substrate provided with first electrically conducting means, the device also comprising second electrically conducting means arranged facing the first electrically conducting means, the first electrically conducting means and the second electrically conducting means possibly being connected to electrical supply means to enable the application of electrostatic forces to the small liquid volume, characterized in that the second electrically conducting means include at least one conducting wire arranged parallel to the substrate and at a fixed distance from the substrate to enable displacement of the small volume of liquid along said conducting wire under the effect of the applied electrostatic forces.

The conducting wire, or the micro-catenary line, performs the first function of acting as an electrode. It also performs a second function, which is to guide the small volumes of liquid. Due to capillarity forces, a droplet present on the micro-catenary line tends to remain in contact with this wire that thus guides it as the droplet displaces.

The device according to the invention is capable of deforming or displacing a small liquid volume by application of a direct or alternating electric field between the micro-catenary line and the first electrically conducting means. The displacement of small volumes of liquid can be explained with reference to prior art mentioned above, and describing the electrostatic forces.

Advantageously, the first electrically conducting means comprise electrodes placed on a non-electrically conducting face of the substrate and parallel to the direction of the conducting wire.

Preferably, the conducting wire is wetting for the small liquid volume. This provides better guidance of the small liquid volume by the micro-catenary line.

The first electrically conducting means and/or the second electrically conducting means may possibly be covered with a layer of electrically insulating material. If the liquid to be displaced is electrically conducting, this enables insertion of an insulating layer so as to not create intense electric currents through the liquid droplet.

The device may include an ambient medium in which the small liquid volume displaces, this ambient medium being composed of a gas or liquid that is not miscible with the small liquid volume. For example, if the liquid to be displaced is composed of an aqueous solution, the ambient medium might be an oil bath. This prevents evaporation of the liquid when a long protocol is applied at high temperature.

According to a first variant embodiment, the determined distance between the conducting wire and the substrate is such that in the absence of any applied electrostatic forces, the small liquid volume is in contact with the substrate, the substrate providing a non-wetting contact with the liquid of the small volume of liquid.

According to a second variant embodiment, the determined distance between the conducting wire and the substrate, and the diameter of the conducting wire, are such that the small volume of liquid is not in contact with the substrate, in the absence of any applied electrostatic forces.

In this case, since the conducting wire is arranged below the substrate, the determined distance between the conducting wire and the substrate may be such that a first value of applied electrostatic forces causes contact between the small liquid volume and the substrate. The substrate can then offer a wetting contact to the small liquid volume so as to transfer the small liquid volume onto the substrate when the applied electrostatic forces are cancelled out or are sufficiently low. The substrate may also provide a hydrophobic contact to the small liquid volume so that the small liquid volume is supported only by the conducting wire when the applied electrostatic forces are cancelled out or are sufficiently low.

According to one particular operating mode, the determined distance between the conducting wire and the substrate and the diameter of the conducting wire are such that the small volume of liquid is not in contact with the substrate, in the presence of the applied displacement electrostatic forces.

The device may comprise means of self-aligning and self-positioning the conducting wire with the means of supplying and removing the small volume of liquid. Advantageously, the means of supplying and removing the small volume of liquid comprises at least one micro-capillary line.

According to a third variant embodiment, the substrate provides a surface with asymmetric roughness to the small volume of liquid, the distance between the conducting wire and the substrate being such that the small volume of liquid is in contact with the substrate under the effect of the applied electrostatic forces, and the substrate, due to its surface with asymmetric roughness, facilitates the displacement of the small liquid volume. The surface with asymmetric roughness may have a saw tooth type profile. The surface provided by the substrate to the small liquid volume may advantageously be unwetting.

However, with the device according to the invention, it is quite possible to envisage the displacement of several droplets on the same micro-catenary line, or to provide several micro-catenary lines for the displacement of series of droplets.

Thus, the first conducting means may comprise a matrix of electrodes forming rows and columns, the second electrically conducting means comprising conducting wires, at each row of electrodes corresponding to a conducting wire.

The first conducting means may also comprise a matrix of electrodes forming rows and columns, the second electrically conducting means comprising a first series of conducting wires and a second series of conducting wires, with a conducting wire in the first series of conducting wires corresponding to each row of electrodes, and a conducting wire in the second series of conducting wires corresponding to each column of electrodes.

The device may comprise means of heating the conducting wire(s). The heating means may be electrical means for circulating an electrical current in the conducting wire(s). Advantageously, the device comprises means of controlling the temperature of the conducting wire(s) starting from a measurement of the electrical resistance of the conducting wire(s).

BRIEF DESCRIPTION OF THE DRAWINGS

The invention will be better understood and other advantages and special features will become clear after reading the following description given as a non-limitative example, accompanied by the attached drawings in which.

DETAILED DESCRIPTION OF EXEMPLARY EMBODIMENTS

Figure 1:
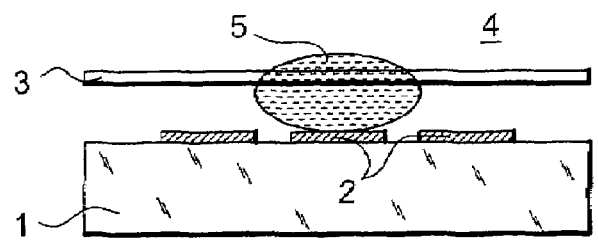
FIG. 1 is a simplified view of a first variant embodiment of a device for displacement of small liquid volumes according to this invention.

The first variant of the invention is shown in FIG. 1. The device shown, that may be called a chip, comprises a plane substrate 1, preferably made of an insulating material. One of the faces of the substrate 1 comprises electrodes 2 aligned along the direction specified for the displacement of micro-droplets. A conducting wire 3 or micro-catenary line is arranged approximately parallel to the substrate 1 and at a determined distance from this substrate. The micro-catenary line 3 is facing the electrodes 2. The assembly is immersed in an ambient medium 4 that may be a gas or a liquid that is not miscible with the liquid in the micro-droplet 5.

The device according to the invention deforms or displaces the droplet 5 by the application of an electric field between the micro-catenary line and at least one of the electrodes 2. The displacement of the droplet can be explained with reference to prior art mentioned above, in relation to electrostatic forces.

Since the micro-catenary line 3 performs a guidance function for the droplet during its displacement, it is preferable if it is wetting for the liquid forming the droplet.

If the liquid forming the droplet is electrically conducting, it is preferable if the electrodes 2 are covered with an insulating layer and/or if the micro-catenary line is coated by an insulating thin layer.

The electric voltage applied between the micro-catenary line and the electrodes to deform or displace the droplet may be direct or alternating.

FIG. 1 shows a single droplet, however it will be quite possible to envisage the displacement of several droplets on the same micro-catenary line.

There are many advantages in the configuration of the device according to the invention. The micro-catenary line performs two functions, firstly an electrical function and secondly a droplet guidance function. Technologically, it is very easy to use. There is no need to confine the droplet between two planes. The micro-catenary line may be very thin, which limits the liquid/solid surface and therefore minimizes chemical, biological or physicochemical interactions (wetting). Bringing the droplet into contact with the micro-catenary line is a means of setting up an electrical configuration favorable to the different principles for displacement of the droplet. Another advantage is that it achieves a component capable of working with several different usage modes that will be described in the following.

In the first variant of the invention shown in FIG. 1, the droplet is always in contact with the surface of the substrate on which the electrodes are fitted. Several electrodes 2 are arranged along the direction of the micro-catenary lines 3.

For example, the substrate is made of glass, but any other type of insulating material such as ceramic or plastic could be used, or a silicon substrate with an insulating layer could be used. This insulating layer may be silicon oxide. The electrodes 2 may be made from a gold or aluminum layer or by any other conducting material. The dimensions of the electrodes may vary from a few tens of $\mu m^2$ up to 1 $mm^2$ depending on the dimensions of the droplets to be transported. The electrode structures may be obtained using conventional micro-technology methods, in other words by photolithography.

The micro-catenary line may be a gold or aluminum or platinum wire, or a wire made of another conducting material. The diameter of the wire may be about 10 $\mu m$ or about 100 $\mu m$. The space between the conducting wire and the substrate may vary from about 10 $\mu m$ to several hundred $\mu m$. Typically, a 25 $\mu m$ diameter gold wire can be used at a distance of about 100 $\mu m$ from the electrodes plane.

The micro-catenary line is connected to a reference potential Vo. A potential V is applied to one of the electrodes 2, and the other electrodes are kept at the reference potential Vo.

It has been verified that the droplet tends to move onto the electrode at which the potential V is applied. This was observed in the case of an insulating liquid such as oil, and with a non-insulating liquid such as salt water. In the latter case, the electrodes 2 have previously been covered by a thin insulating layer of parylene about one $\mu m$ thick, or an insulating material such as silicon oxide ($SiO_2$), silicon nitride ($Si_3N_4$) or Teflon®.

By activating the different electrodes in turn, the droplet can be displaced. The displacement can be explained with reference to prior art. Activation voltages are a few hundred volts. The activation voltage can be reduced as the surface of the substrate on which the electrodes are placed becomes less wetting. Similarly, the activation voltage can be reduced as the distance between the electrodes is reduced. For example, the distance between the electrodes is a few $\mu m$.

Figure 2:
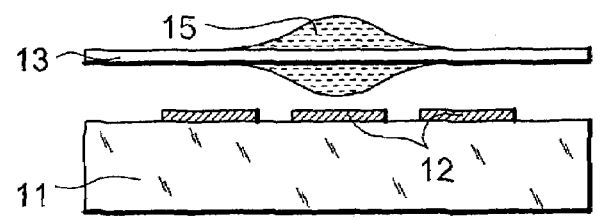
FIG. 2 shows a simplified view of a second variant embodiment of a device for displacement of small liquid volumes according to this invention.

A second variant of the invention is shown in FIG. 2. This variant is identical to the previous variant in terms of technological production. However, in this case the droplet 15 is attached to the micro-catenary line 13 without being in contact with the electrodes 12 present on the substrate 11. It is preferable if the surface of the micro-catenary line 13 is made wetting for the liquid forming the droplet to give good attachment. Similarly, the electrodes 12 may be covered by an insulating layer. It is also preferable to have a catenary diameter of about 100 $\mu m$ so that capillarity forces are sufficiently large compared with gravity forces. Thus, droplets with reasonable dimensions may be attached to the micro-catenary line. For example, a droplet consisting of several microliters of oil may be attached to a 300 $\mu m$ wide catenary line.

It has been confirmed that applying an electrical voltage between the micro-catenary line 13 and one of the electrodes 12 placed close to the droplet 15 causes a deformation of the droplet. This deformation tends to attract the droplet towards the activated electrode.

In this way, by arranging several electrodes 12 on the substrate 11 and by aligning the electrodes along the direction of the micro-catenary line 13, it has been observed that it is possible to displace a droplet by applying an electrical voltage in turn between the different electrodes and the micro-catenary line. Thus, in this case, the droplet moves while remaining supported by the micro-catenary line without having been in contact with the substrate or the electrodes. Therefore in this specific case, there is no constraint on the wetting properties of the surface of the substrate.

The article "Gouttes, bulles, perles et ondes" (Droplets, bubbles, beads and waves) by P. G. de Gennes et al, Editions Belin, 2002, page 19, contains a description of the undulating shape of a wetting droplet on a fiber. It has also been observed that the shape of the droplet can vary depending on its dimensions, when gravity is no longer negligible. The droplet tends to hang below the catenary line. In the case shown in FIG. 2, electrostatic forces are additional to gravity. Thus, it is preferable to turn the system over such that electrostatic forces oppose gravity to avoid risks of the droplet becoming detached from the micro-catenary line. This is shown in FIG. 3.

Figure 4:
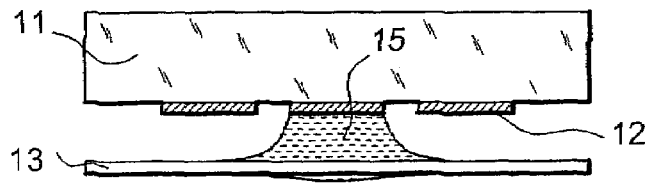
FIGS. 4 and 5 illustrate an operating method of the device in FIG. 3, FIGS. 6A and 6B show a simplified view of a third variant embodiment of a device for displacement of small liquid volumes according to this invention.

If the activation voltage is increased, the droplet may deform until it touches the activation electrode, as shown in FIG. 4.

Figure 3:
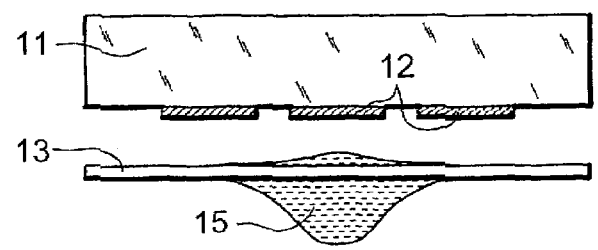
FIG. 3 shows a simplified view of a particular use of the device in the second variant embodiment.
Figure 5:
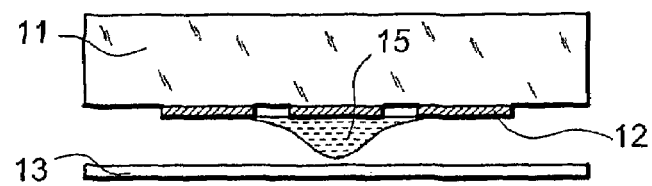

If the activation voltage is reduced or eliminated, one of the following two scenarios may arise:
  if the electrode 12 is wetting (see FIG. 5), the droplet 15 will naturally remain attached to the surface by capillarity forces, and the process is then irreversible;
  if the surface of the electrode 12 is very hydrophobic, the droplet will unwet the surface to return to the position illustrated in FIG. 3, and in this case the process is reversible, in other words contact between the droplet and the activation electrode can be imposed whenever it is desired by varying the activation voltage.

Thus, depending on the dimensions and the wetting properties, it is possible to either transfer the drop from the micro-catenary line to the substrate, or temporarily impose wetting of the drop on the surface of the substrate.

In conclusion, with the device according to the invention, the drop can be displaced along the micro-catenary line with the following two possibilities:
  the droplet slides and always remains in contact with the surface of the substrate,
  the droplet moves without coming into contact with the surface of the substrate. In this case, for example after a contact free displacement over a given length of the catenary line, the droplet may temporarily be spread on the surface of the substrate, or the droplet may be transferred from the micro-catenary line to the surface of the substrate.

Figures 6A, 6B:
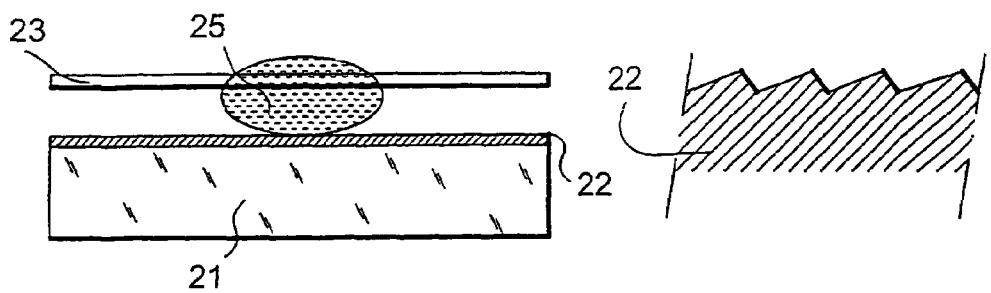

Part A in FIG. 6 shows a third variant of the invention. The substrate 21 is made from a conducting material or is covered by a conducting layer 22. It is also preferable to deposit an insulating layer not shown in FIG. 6) on the surface of the substrate (or the conducting layer) in contact with the droplet. Furthermore, this surface has an asymmetric roughness (for example with a saw tooth type profile), as shown in part B in FIG. 6).

The surface of the substrate (or the surface of the conducting layer) in contact with the droplet is advantageously made not wetting by the droplet 25. The droplet 25 is attached to the micro-catenary line 23, and is also fixed on the surface of the substrate or the conducting layer. Application of an alternating voltage between the micro-catenary line and the conducting layer 22 can make the droplet 25 vibrate. It has been verified that the droplet 25 can be displaced along the micro-catenary line 23. This can be explained with reference to the article "Moving droplets in asymmetrically structured surfaces" mentioned above.

Figure 7:
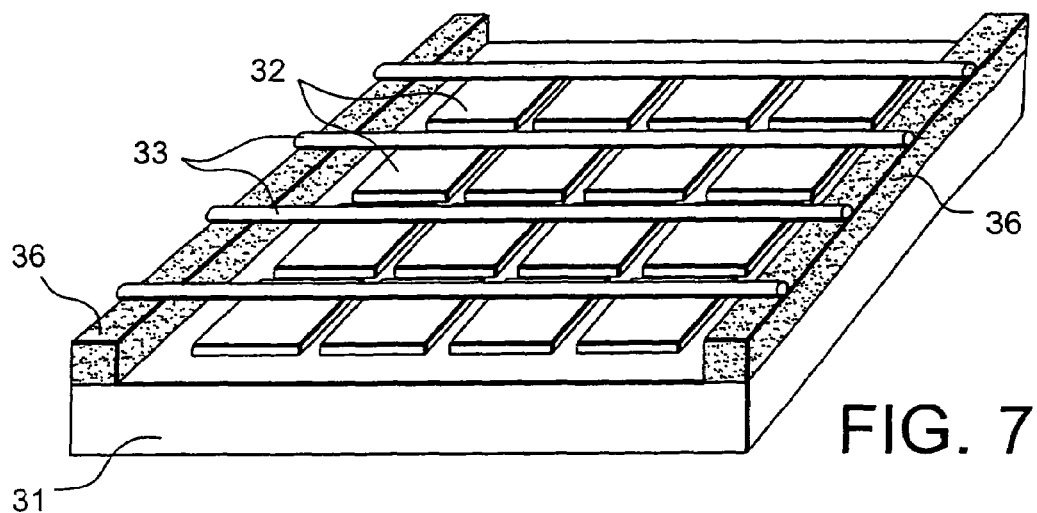
FIG. 7 shows a device for displacement of small liquid volumes with several micro-catenary lines, according to this invention.

Another aspect of the invention is shown in FIG. 7. The substrate 31 supports an electrodes matrix 32, distributed in rows and in columns and that can be covered by an insulating layer (not shown). Several micro-catenary lines 33 are put in parallel along the rows of the electrodes. The micro-catenary lines 33 are placed at a given distance from the surface of the substrate by means of spacers 36. In this way, it is possible to work in parallel on several rows of electrodes and to displace several droplets using one of the methods described above.

Figure 8:
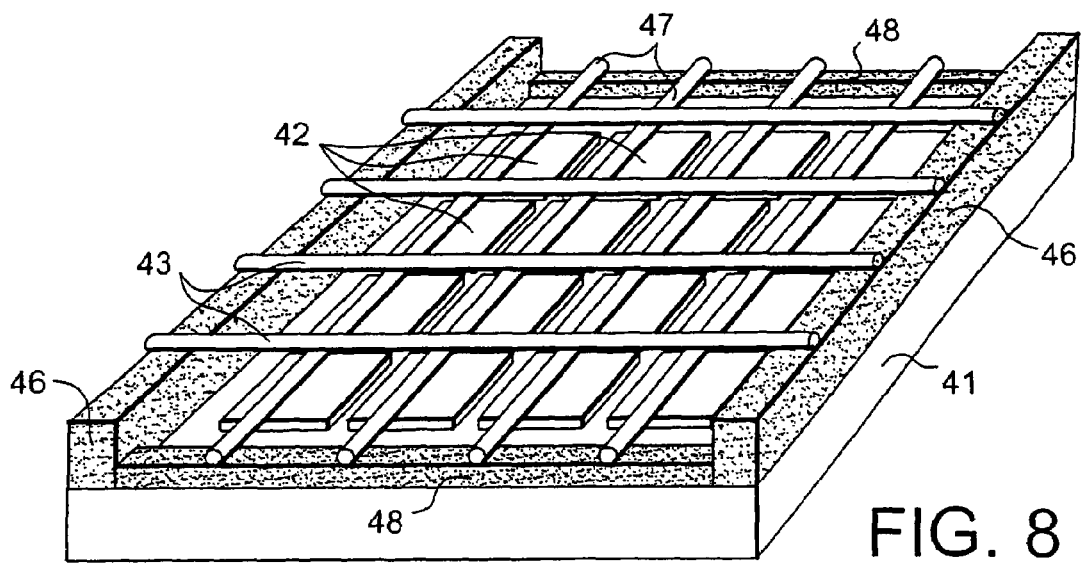
FIG. 8 shows a device for displacement of small liquid volumes comprising two series of intersecting micro-catenary lines according to this invention.

Another aspect of the invention is shown in FIG. 8. The substrate 41 supports a matrix of electrodes 42, distributed in rows and in columns that can be covered with a thin insulating layer (not shown). A first series of micro-catenary lines 43 is put in parallel along the rows of electrodes. The micro-catenary lines 43 are placed at a given distance from the surface of the substrate by means of spacers 46. A second series of micro-catenary lines 47 is put in parallel but placed perpendicular to the series of micro-catenary lines 43, in other words along the direction of the columns of electrodes. The micro-catenary lines 47 are placed at a given distance from the surface of the substrate by means of spacers 48. The spacers 46 and 48 may be at different heights. Thus, the droplets can be moved along two perpendicular directions.

Figure 9:
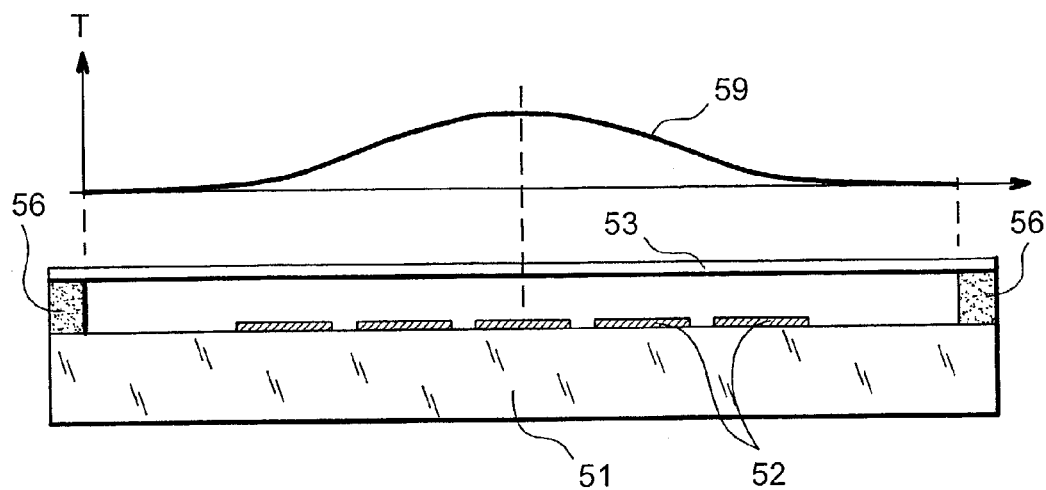
FIG. 9 shows a device with temperature-controlled micro-catenary lines for displacement of small volumes of liquid.

Another aspect of the invention consists of using the micro-catenary line to heat a droplet of liquid. This can be achieved very easily by the Joule effect, by circulating an electric current along the micro-catenary line. This is shown diagrammatically in FIG. 9. This figure shows an insulating substrate 51 supporting electrodes 52 aligned facing a micro-catenary line 53 supported by spacers 56. The droplet can be brought to an arbitrary position on the micro-catenary line 53 by one of the processes described above. Preferably, the droplet will be placed at the middle of the micro-catenary line. Due to the symmetry of the system, the temperature profile T of the micro-catenary line has a bell shape shown diagrammatically by the curve 59. It is well known that the resistivity of the electric material generally depends on the temperature. Thus, it is easy to check the temperature of the system simply by measuring the resistance of the micro-catenary line.

The advantage of this system is that it produces a catenary-droplet system with a very low thermal mass, which is not the case in prior art in which reactions take place in liquids placed in contact with heat sinks or ducts. Thus, it is easy to heat the droplet or allow it to cool within very short times. This is useful for some biological protocols requiring temperature cycling, such as PCR (see the article "Miniaturized flow-through PCR with different template types in a silicon chip thermocycler" mentioned above).

We will now describe embodiments of devices according to the invention.

Figure 10:
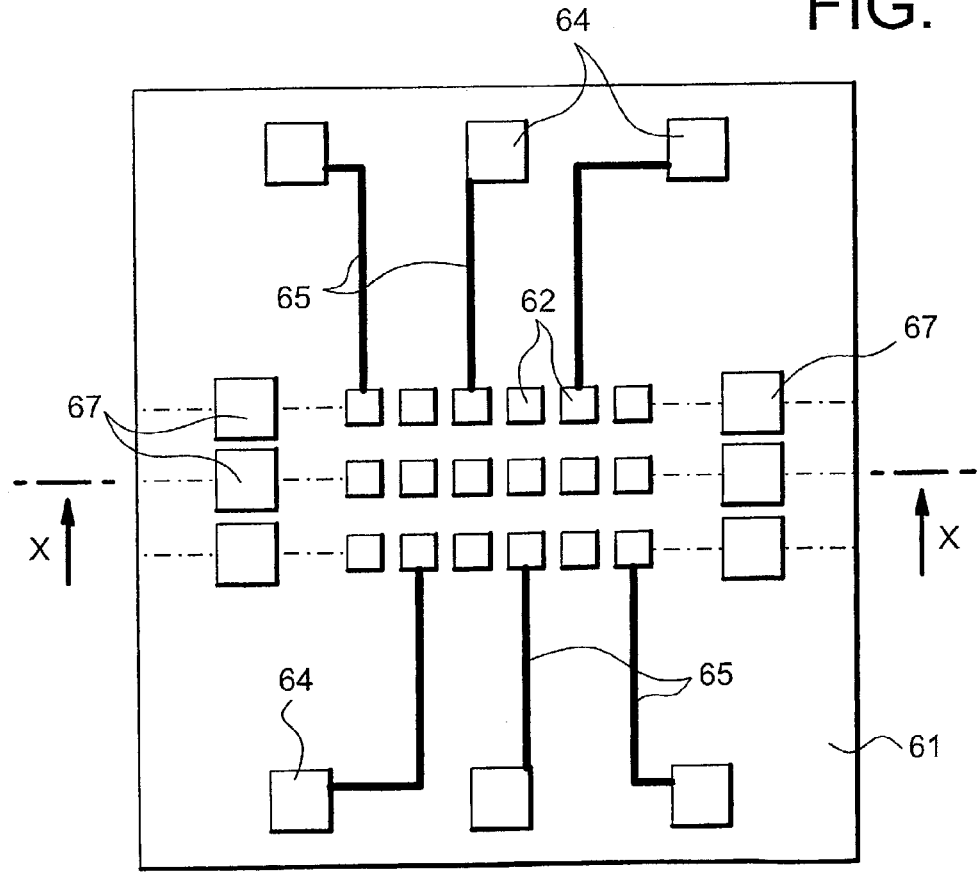
FIG. 10 shows a top view of a device for displacement of small liquid volumes according to the invention, during manufacture.

FIG. 10 shows a top view of the device according to a first embodiment, during manufacturing. FIGS. 11A to 11F illustrate steps in the manufacturing process according to this first embodiment.

The device comprises a substrate 61 made of glass, silica, plastic or silicon covered by an insulating layer. A conducting layer 60, for example made of gold, aluminum or ITO (see FIG. 11A), is deposited on this substrate. This conducting layer 60 is structured by a photolithography step in order to define a matrix of electrodes 62 connected to pads 64 through rows 65 (see FIGS. 10 and 11B). The dimension of the electrodes varies from a few tens to a few hundred µm (typically 500 µm by 500 µm). The spacing between each electrode is a few µm (5 to 10 µm). The structure of the conducting layer also leads to pads 67 being arranged on each side of the rows of electrodes 62. The substrate is then covered by a layer 68 of an insulating material such as silicon oxide or $Si_3N_4$, with a thickness of the order of 0.1 to 1 µm (see FIG. 11C). A step to etch the insulating layer located on pads 64 and 67 will enable resumption of the electrical contact (see FIG. 11D).

A thick resin (for example the EPON SU8 Epoxy Resin, see American U.S. Pat. No. 4,882,245) is then deposited and is structured by photolithography to make the spacers 66. The thickness of the layer forming the spacer varies from a few tens to a few hundred µm (see FIG. 11E).

The substrate is cut out to obtain individualized chips (a single chip being shown in FIGS. 10 and 11A to 11E for simplification reasons). Micro-technological processes are then used to make a large number of components on a 100 mm diameter disk. Each chip is glued to a support 69 as is frequently done in microelectronics (see FIG. 11F). All that remains is to make electrical bridges 70 between the pads 64 or 67 and the connection pads of the support 69 by using an electrical soldering machine like that frequently used in microelectronics. The same machine can also be used to make micro-catenary lines 63 between two opposite pads 67 on the same row of electrodes 62. For example, the connection wires used in soldering machines may be gold or aluminum wires with a diameter of a few tens of µm (for example 25 µm). A particular material will be chosen for the micro-catenary line depending on the application, for example gold and aluminum have different wetting properties.

Figure 11D:
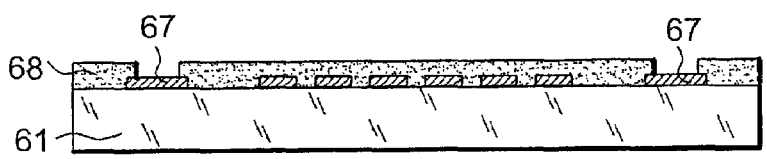
Figure 11E:
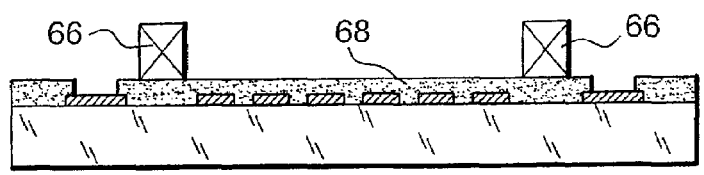
Figure 11F:
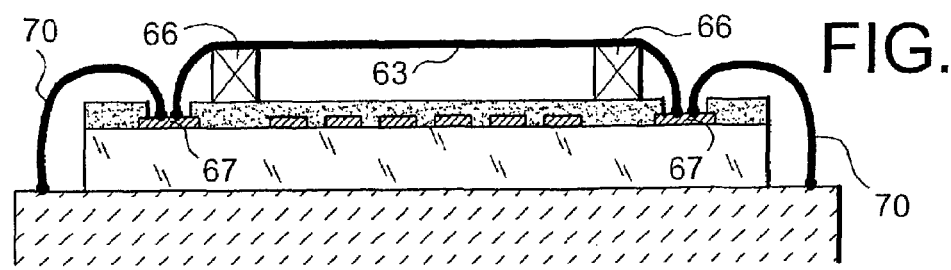
Figure 12A:
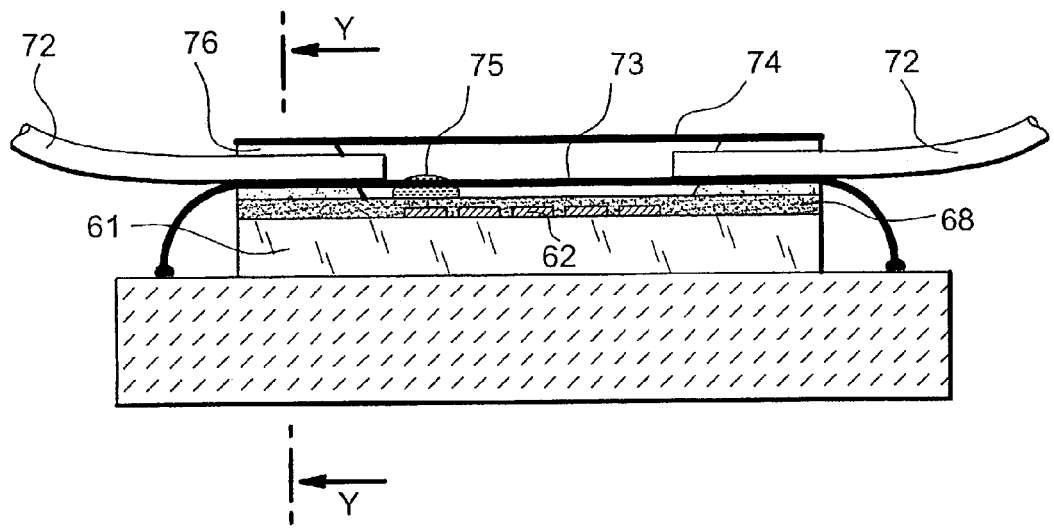
Figure 12B:
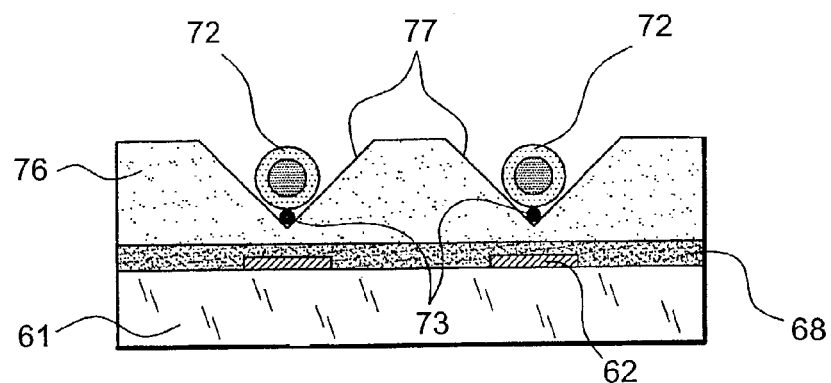

One variant embodiment is shown in FIGS. 12A and 12B, FIG. 12B being a sectional view along the YY axis in FIG. 12A. The spacer is made by micro-machining a substrate 76 assembled to the substrate 61 equipped as shown in FIG. 11D. The substrate 76 comprises a grooving system 77 that helps to self-align and self-position the micro-catenary line 73 with very high precision. For example, the grooves may be formed by anisotropic etching in a substrate made of monocrystalline silicon.

The component made can be confined, for example to limit evaporation, by covering the component by a film 74, if desired. A simple self-sticking film can be used.

The droplets 75 can be injected in different ways. A drop dispensing system (printer head) can be used. The self-sticking film 74 can also be perforated by a needle, and drops may be injected with this needle. The self-sticking film then acts as a septum. Another solution is to use the grooving system again to position the micro-capillary lines 72. Thus, the ends of the micro-capillary lines 72 are naturally placed close to the corresponding micro-catenary lines 73 and are self-aligned with them. For example, the injection of liquids can be controlled by a syringe push connected to the other end of the micro-capillary lines or by using a pressurized system.

A second embodiment is illustrated firstly by FIGS. 13A to 13D, and secondly by FIGS. 14A to 14E. In this embodiment, the micro-catenary line is micro-machined directly in a second substrate.

Figure 13A:
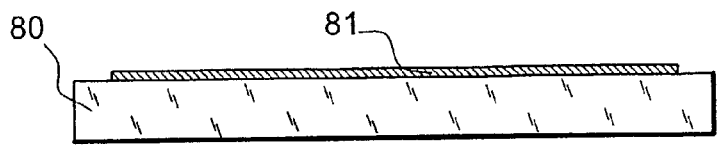
FIGS. 13A to 13D illustrate the process for manufacturing another device for displacement of small liquid volumes according to the invention.
Figure 13B:
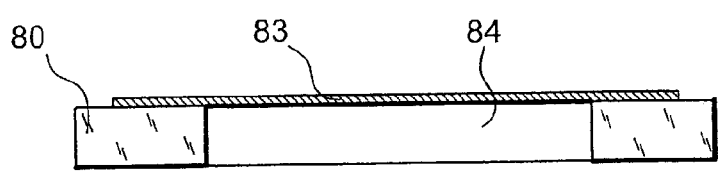
Figure 13C:
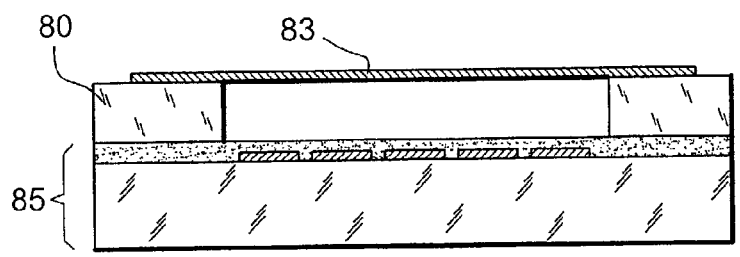
Figure 13D:
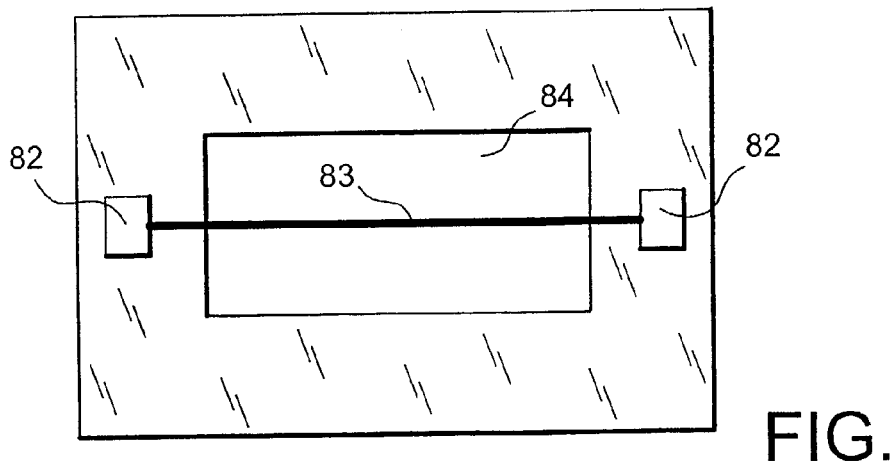

FIGS. 13A to 13C are side and sectional views. FIG. 13D is a top view corresponding to FIG. 13B.

FIG. 13A shows a support 80 forming the second substrate. A conducting layer 81 is deposited on one face of the second substrate 80. A photo-lithoengraving step is carried out to define the form of the micro-catenary line and its connection pads. FIG. 13D shows the shape applied to the micro-catenary line 83 and its connection pads 82.

The second substrate 80 is then etched to define an opening 84 releasing the micro-catenary line 83 (see FIGS. 13B and 13D). FIG. 14D is a top view on plane DD shown in FIG. 14C without the layer 96.

Figure 11A:
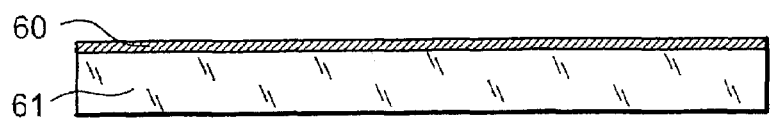
FIGS. 11A to 11F are views corresponding to section XX in FIG. 10 and illustrate the process for manufacturing the device corresponding to FIG. 10, FIGS. 12A and 12B are longitudinal and transverse sectional views respectively of another device for displacement of small liquid volumes according to the invention.
Figure 11B:
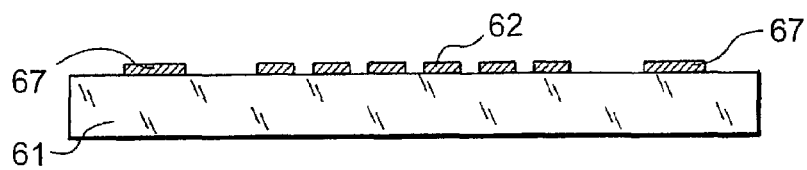
Figure 11C:

The second substrate 80 thus machined is fixed to a structure 85 of the type shown in FIG. 11C. It is solidarized such that the micro-catenary line 83 is deposited facing a row of activation electrodes (see FIG. 13C). Electrical connections to the micro-catenary line are not shown.

FIGS. 14A, 14B, 14C and 14E are side and sectional views. FIG. 14D is a top view corresponding to plane DD in FIG. 14C.

Figure 14A:
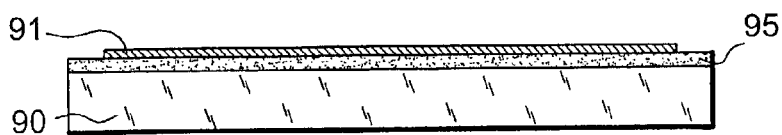
FIGS. 14A to 14E illustrate the process for manufacturing yet another device for displacement of small liquid volumes according to the invention.
Figure 14B:
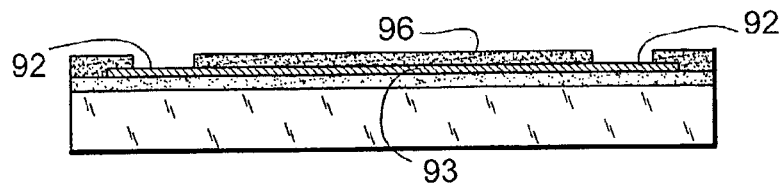

FIG. 14A shows a support 90 forming the second substrate. An insulating layer 95 and a conducting layer 91 are successively deposited on a face of the second substrate 90. A photo-lithography step is used to define the shape of the micro-catenary line and its connection pads. FIG. 14D shows the shape applied to the micro-catenary line 93 and its connection pads 92.

Another layer is deposited on the second substrate 90 by covering the micro-catenary line. Another photo-lithography step is carried out to define the shape of this layer and the shape of the layer 93 to reveal the connection pads 92 and to leave a narrow band 96 remaining on the micro-catenary line 93 and a narrow band under the micro-catenary line 93 (see FIG. 14B).

Figure 14C:
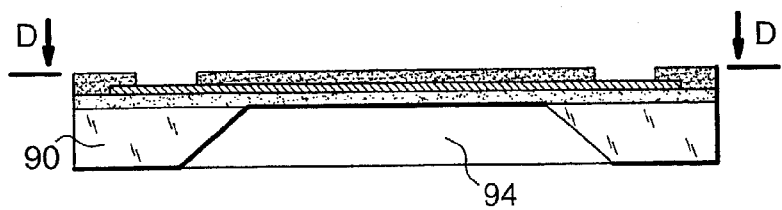
Figure 14D:
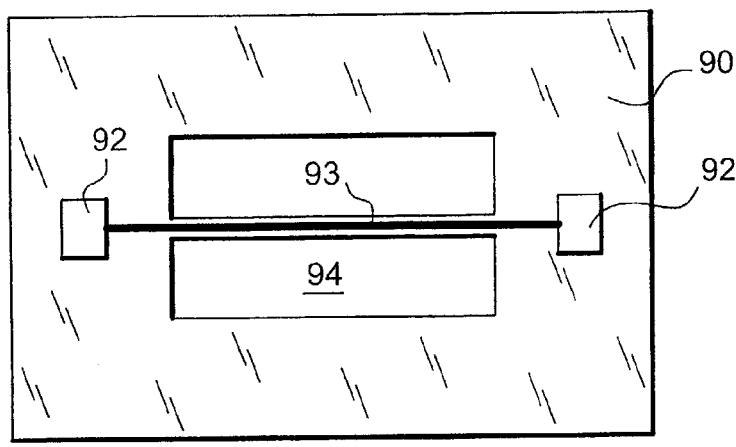
Figure 14E:
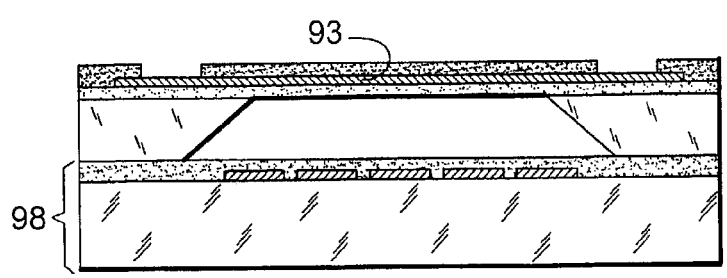

An etching operation is then performed starting from the back face of the second substrate 90 to obtain an opening 94 (see FIGS. 14C and 14D). FIG. 14D is a top view along plane DD shown in FIG. 14C and without layer 96.

The second substrate thus machined is fixed to a structure 98 of the type shown in FIG. 11C. It is fixed such that the micro-catenary line 93 is placed facing a row of activation electrodes (see FIG. 14E). The electrical connections to the micro-catenary line are not shown.

In this case, the micro-catenary line is included between two layers acting as a mechanical support. The layers 95 and 96 may be made from a pre-tensioned material to stretch and stiffen the micro-catenary line. This can be achieved from a second silicon substrate 90 on which the silicon nitride layers 95 and 96 have been deposited by a PECVD process for checking the stress level in the deposited material. With this embodiment, the micro-catenary line can be coated with an insulating material.

Therefore, the use of micro-technologies makes it possible to structure micro-catenary lines by a stack of different layers. Different shapes of micro-catenary lines can also be drawn.

Figure 15:
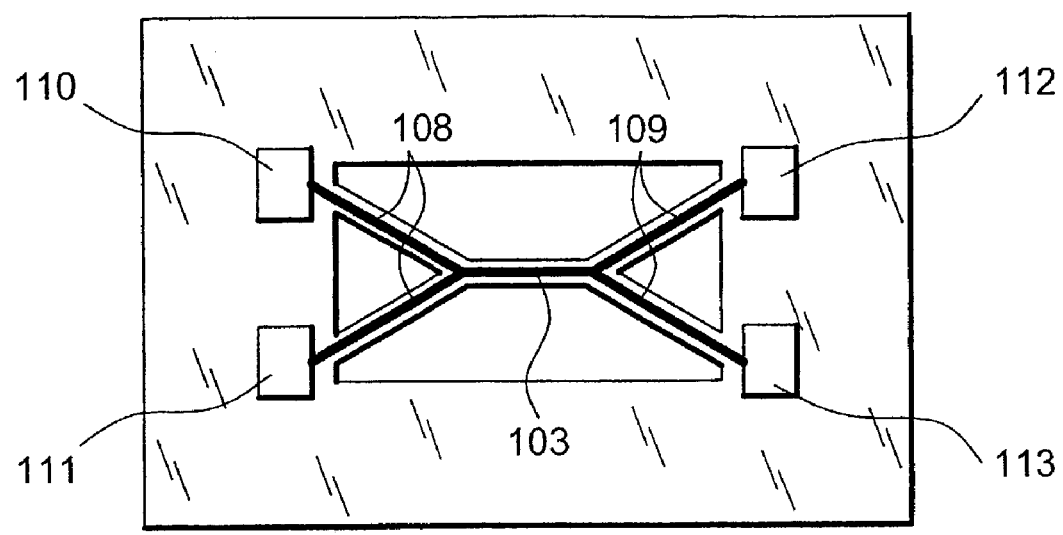
FIG. 15 is a top view of a device for displacement of small liquid volumes, using switchings according to the invention.

Thus, FIG. 15 is a top view of a device according to the invention showing a micro-catenary line 103 provided with a first switch 108 and a second switch 109. The first switch 108 is connected to connection pads 110, 111 and the second switch 109 is connected to connection pads 112, 113. Note that the micro-catenary line 103 and the switches 108 and 109 are arranged on a mechanical support. The switches are used to mix, sort or break droplets into fragments.

Figure 16:
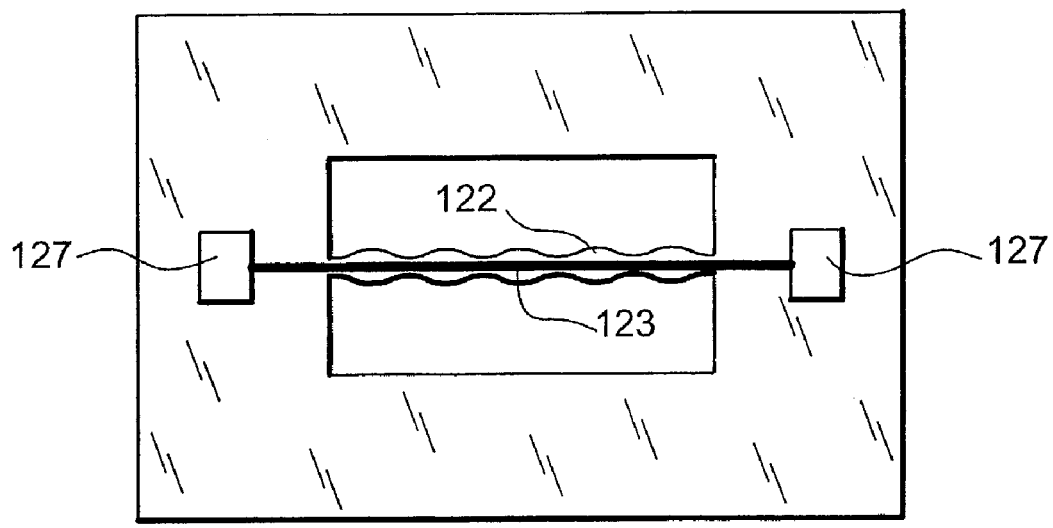
FIG. 16 is a top view of a device for displacement of small liquid volumes, with preferred positions for the small liquid volumes according to the invention.

FIG. 16 is a top view of a device according to the invention showing a micro-catenary line 123 connected to connection pads 127. The micro-catenary line 123 is arranged on a support 122 with an undulating shape to facilitate positioning of the droplets on the micro-catenary line by capillarity forces.

The invention claimed is:

1. Device for displacement of at least a small volume of liquid under the effect of an electrical control, including a substrate provided with first electrically conducting means, the device also comprising second electrically conducting means arranged facing the first electrically conducting means, the first electrically conducting means and the second electrically conducting means being connected to electrical supply means to enable the application of electrostatic forces to the small liquid volume, characterized in that the second electrically conducting means include at least one conducting wire arranged parallel to the substrate and at a fixed distance from the substrate to enable displacement of the small volume of liquid along said conducting wire under the effect of the applied electrostatic forces.

2. Device according to claim 1, wherein the first electrically conducting means comprise electrodes placed on a non-electrically conducting face of the substrate and parallel to the direction of the conducting wire.

3. Device according to claim 1, wherein the conducting wire is wetting for the small liquid volume.

4. Device according to claim 1, wherein the first electrically conducting means and/or the second electrically conducting means are covered with a layer of electrically insulating material.

5. Device according to claim 1, further including an ambient medium in which the small liquid volume displaces, the ambient medium being composed of a gas or liquid that is not miscible with the small liquid volume.

6. Device according to claim 5, wherein the liquid that is not miscible with the small liquid volume is an oil bath.

7. Device according to claim 1, wherein the determined distance between the conducting wire and the substrate is such that the small volume of liquid is in contact with the substrate in the absence of any applied electrostatic forces, the substrate providing a non-wetting contact with the small volume of liquid.

8. Device according to claim 1, wherein the determined distance between the conducting wire and the substrate, and the diameter of the conducting wire, are such that the small volume of liquid is not in contact with the substrate, in the absence of any applied electrostatic forces.

9. Device according to claim 1, wherein the determined distance between the conducting wire and the substrate, and the diameter of the conducting wire, are such that the small volume of liquid is not in contact with the substrate, in the absence of any applied electrostatic forces.

10. Device according to claim 8, wherein since the conducting wire is arranged below the substrate, the determined distance between the conducting wire and the substrate is such that a first value of applied electrostatic forces causes contact between the small liquid volume and the substrate.

11. Device according to claim 10, wherein the substrate offers a wetting contact to the small liquid volume so as to transfer the small liquid volume onto the substrate when the applied electrostatic forces are cancelled out or are sufficiently low.

12. Device according to claim 10, wherein the substrate provides a hydrophobic contact to the small liquid volume so that the small liquid volume is supported only by the conducting wire when the applied electrostatic forces are cancelled out or are sufficiently low.

13. Device according to claim 1, further comprising means of self-aligning and self-positioning the conducting wire with the means of supplying and/or removing the small volume of liquid.

14. Device according to claim 13, wherein the means of supplying and/or removing the small volume of liquid comprise at least one micro-capillary.

15. Device according to claim 1, wherein the substrate provides a surface with asymmetric roughness to the small volume of liquid, the distance between the conducting wire and the substrate being such that the small volume of liquid is in contact with the substrate under the effect of the applied electrostatic forces, and the substrate, due to its surface with asymmetric roughness, facilitates the displacement of the small liquid volume.

16. Device according to claim 15, wherein the surface with asymmetric roughness has a saw tooth type profile.

17. Device according to claim 15, wherein the surface provided by the substrate to the small liquid volume is non-wetting.

18. Device according to claim 1, wherein the first conducting means may comprise a matrix of electrodes forming rows and columns, the second electrically conducting means comprising conducting wires, at each row of electrodes corresponding to a conducting wire.

19. Device according to claim 1, wherein the first conducting means may also comprise a matrix of electrodes forming rows and columns, the second electrically conducting means comprising a first series of conducting wires and a second series of conducting wires, with a conducting wire in the first series of conducting wires corresponding to each row of electrodes, and a conducting wire in the second series of conducting wires corresponding to each column of electrodes.

20. Device according to claim 1, further comprising means of heating the conducting wire(s).

21. Device according to claim 20, wherein the heating means are electrical means for circulating an electrical current in the conducting wire(s).

22. Device according to claim 21, further comprising means of controlling the temperature of the conducting wire(s) starting from a measurement of the electrical resistance of the conducting wire(s).

* * * * *